(12) United States Patent
Yoshida et al.

(10) Patent No.: US 9,241,615 B2
(45) Date of Patent: Jan. 26, 2016

(54) IMAGE ACQUISITION AND DISPLAY METHOD AND IMAGE CAPTURING AND DISPLAY APPARATUS

(75) Inventors: Koji Yoshida, Kanagawa-ken (JP); Masayuki Iwasaka, Kanagawa-ken (JP)

(73) Assignee: FUJIFILM CORPORATION, Tokyo (JP)

( * ) Notice: Subject to any disclaimer, the term of this patent is extended or adjusted under 35 U.S.C. 154(b) by 852 days.

(21) Appl. No.: 13/212,954

(22) Filed: Aug. 18, 2011

(65) Prior Publication Data

US 2012/0050514 A1 Mar. 1, 2012

(30) Foreign Application Priority Data

Aug. 31, 2010 (JP) ................................. 2010/195025

(51) Int. Cl.
| H04N 9/47 | (2006.01) |
| A61B 1/06 | (2006.01) |
| A61B 1/00 | (2006.01) |
| A61B 1/04 | (2006.01) |
| A61B 1/07 | (2006.01) |
| A61B 5/00 | (2006.01) |

(52) U.S. Cl.
CPC ............... *A61B 1/063* (2013.01); *A61B 1/0005* (2013.01); *A61B 1/043* (2013.01); *A61B 1/0638* (2013.01); *A61B 1/07* (2013.01); *A61B 5/0071* (2013.01); *A61B 5/0084* (2013.01)

(58) Field of Classification Search
CPC ...... A61B 1/041; A61B 7/18; A61B 1/00036; A61B 1/0005; A61B 19/52
USPC ........................................................ 348/77
See application file for complete search history.

(56) References Cited

U.S. PATENT DOCUMENTS

| 6,307,957 | B1* | 10/2001 | Gutkowicz-Krusin et al. ............................ 382/128 |
| 6,468,204 | B2 | 10/2002 | Sendai et al. |
| 2005/0261710 | A1* | 11/2005 | Sakamoto et al. ............ 606/139 |
| 2009/0028407 | A1* | 1/2009 | Seibel et al. ................... 382/131 |
| 2009/0287060 | A1* | 11/2009 | Pell et al. ....................... 600/201 |
| 2010/0008467 | A1* | 1/2010 | Dussault et al. ................ 378/65 |
| 2010/0042084 | A1 | 2/2010 | Nariyuki et al. |

FOREIGN PATENT DOCUMENTS

| JP | 2002-28125 (A) | 1/2002 |
| JP | 2002-253480 (A) | 9/2002 |
| JP | 2003-339644 (A) | 12/2003 |
| JP | 2004-24656 (A) | 1/2004 |

(Continued)

OTHER PUBLICATIONS

Notice of Grounds for Rejection dated Oct. 15, 2013, with English translation.

(Continued)

*Primary Examiner* — William C Vaughn, Jr.
*Assistant Examiner* — Daniel Tekle
(74) *Attorney, Agent, or Firm* — McGinn IP Law Group, PLLC

(57) ABSTRACT

Identifying, based on a special image, a prescribed region of interest in a special image, determining a boundary line of an area which includes a region in an ordinary image corresponding to the identified region of interest and a predetermined margin added to the region, and displaying a boundary line of the region and the boundary line of the area in the ordinary image.

18 Claims, 8 Drawing Sheets

(56) References Cited

FOREIGN PATENT DOCUMENTS

| JP | 2010-42182 (A) | 2/2010 |
| JP | 2010-82041 (A) | 4/2010 |

OTHER PUBLICATIONS

Chinese Office Action dated Jun. 26, 2014 with English Translation.
Chinese Office Action dated Mar. 9, 2015 with English translation.

* cited by examiner

| IMAGING REGION | SURGICAL MARGIN |
|---|---|
| LUNG | X1 |
| LIVER | X2 |
| STOMACH | X3 |
| ⋮ | ⋮ |

FIG.12
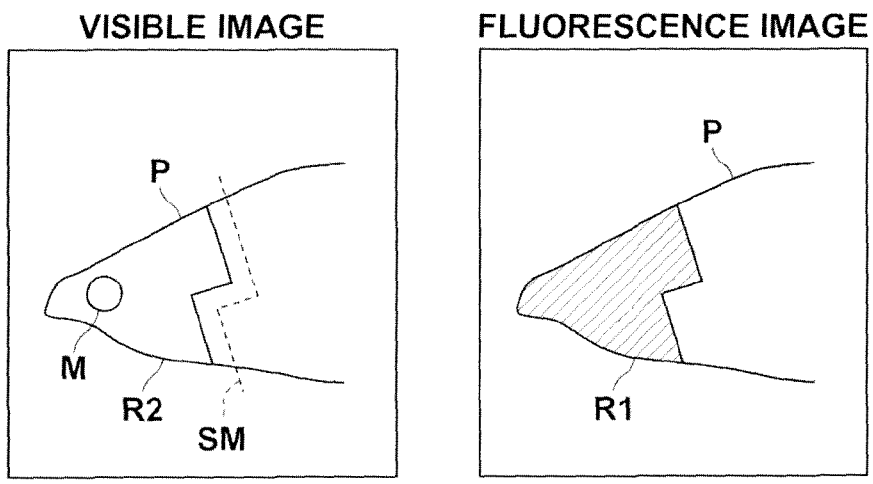
FIG.13
| RESECTION TOOL | DISPLAY METHOD |
|---|---|
| ELECTROSURGICAL KNIFE | DISPLAY A |
| STAPLER | DISPLAY B |
| ⋮ | ⋮ |
FIG.14
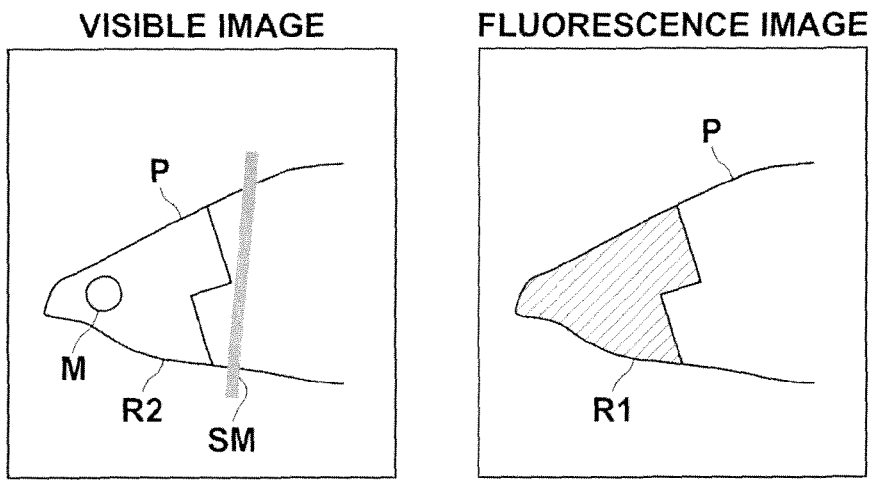

IMAGE ACQUISITION AND DISPLAY METHOD AND IMAGE CAPTURING AND DISPLAY APPARATUS

BACKGROUND OF THE INVENTION

1. Field of the Invention

The present invention relates to an image acquisition and display method and an image capturing and display apparatus for obtaining an ordinary image and a special image by projecting illumination light and special light onto an observation area and displaying the obtained ordinary and special images. More particularly, the invention relates to an auxiliary function to assist resection of a portion of the observation area in surgery or the like.

2. Description of the Related Art

Endoscope systems for observing tissues of body cavities are widely known, and electronic endoscope systems for capturing an ordinary image of an observation area in a body cavity by projecting white light onto the observation area and displaying the captured ordinary image on a monitor screen are widely used.

Further, as one of such endoscope systems, a system in which ICG (indocyanine green) is administered to an observation area in advance in order to observe, for example, a blood vessel run, blood flow, lymphatic vessel, lymph flow, bile duct run, or bile flow under fat which does not appear in an ordinary image and an ICG florescence image is captured by projecting near infrared excitation light to the observation area is proposed.

The use of such endoscope systems that capture a fluorescence image allows a lesion site, such as a tumor, in the observation area to be identified, and there may be a case that the identified tumor portion or an organ section which includes the tumor portion is desired to be resected.

When resecting a tumor or the like, it is necessary to remove the tumor area or an organ section with an added surgical margin so that no cancer cell exits in the remaining portion of the organ after surgery.

The extent of resection, including the surgical margin described above, may not be recognized, however, by simply identifying the tumor or the like in a fluorescence image.

Further, when resecting a tumor or the like, the resection is performed by observing an ordinary image of white light to begin with. Thus, even if the extent of a tumor is identified in a fluorescence image, the extent of resection, including the surgical margin, may not be recognized in the ordinary image and an appropriate resection procedure may not be performed.

Although, it is proposed, in Japanese Unexamined Patent Publication No. 2010-082041, that a surgical margin is displayed in an image obtained by an endoscope, this surgical margin is a margin simply set in advance and not a surgical margin determined based on a tumor identified in a fluorescence image captured in real time as described above.

Further, U.S. Pat. No. 6,468,204 describes that a boundary of a tumor is identified and visualized in real time using a fluorescence image captured during a surgical operation, but the surgical margin described above is not taken into consideration at all.

The present invention has been developed in view of the circumstances described above, and it is an object of the invention to provide an image acquisition and display method and an image capturing and display apparatus capable of displaying an ordinary image that allows a tumor or the like to be removed to an appropriate extent, including a surgical margin, in an endoscope system for capturing a fluorescence image like that described above.

SUMMARY OF THE INVENTION

An image acquisition and display method of the present invention is a method for obtaining an ordinary image captured by projecting illumination light onto an observation area and receiving reflection light reflected from the observation area and a special image captured by projecting special light onto the observation area and receiving light emitted from the observation area, and displaying the obtained ordinary and special images, the method including the steps of:

identifying, based on the special image, a prescribed region of interest in the special image;

determining a boundary line of an area which includes a region in the ordinary image corresponding to the identified region of interest and a predetermined margin added to the region; and displaying a boundary line of the region and the boundary line of the area in the ordinary image.

An image capturing and display apparatus of the present invention is an apparatus, including:

a light projection unit for projecting illumination light and special light onto an observation area;

an imaging unit for imaging an ordinary image by receiving reflection light reflected, by the projection of the illumination light, from the observation area and a special image by receiving light emitted, by the projection of the special light, from the observation area;

a display unit for displaying the ordinary and special images;

a region of interest identification unit for identifying, based on the special image, a prescribed region of interest in the special image; and a margin determination unit for determining a boundary line of an area which includes a region in the ordinary image corresponding to the identified region of interest and a predetermined margin added to the region, wherein the display unit displays a boundary line of the region and the boundary line of the area in the ordinary image.

In the image capturing and display apparatus of the present invention, the region of interest identification unit may be a unit that determines the region of interest based on section information preset based on biological information of the observation area.

Further, the imaging unit may be a unit that captures an ordinary image which includes a marker image of a length measurement marker having preset length information and the margin determination unit may be a unit that determines the margin based on a size of the marker image.

The length measurement marker may have a blue or green color.

Further, the observation area may be a living body and the length measurement marker may be a marker made of a bioabsorbable material and placed on the living body.

Still further, the observation area may be a living body and the margin determination unit may be a unit that determines the margin according to a region of the living body.

Further, the observation area may be a living body and the display unit may be a unit that changes display form of the boundary line of the area according to preset information of resection tool for resecting the living body.

Still further, the apparatus may further include a table that relates information of a plurality of resection tools to display forms of the boundary line of the area.

Further, the light projection unit may be a unit that projects excitation light as the special light and the imaging unit may be a unit that captures a fluorescence image as the special image by receiving fluorescence emitted, by the projection of the excitation light, from the observation area.

According to the image acquisition and display method, and image capturing and display method of the present invention, based on a special image, a prescribed region of interest is identified in the special image, then a boundary line of an area which includes a region in an ordinary image corresponding to the identified region of interest and a predetermined margin added to the region is determined, and a boundary line of the region and the boundary line of the area are displayed in the ordinary image. This enables a doctor or the like to remove a tumor or the like to an appropriate extent, including a surgical margin, by observing the boundary lines in the ordinary image.

BRIEF DESCRIPTION OF THE DRAWINGS

FIG. 12 illustrates a display example in which a section R1 is identified in a fluorescence image of lung P, and a section R2 and boundary line SM of a surgical margin are displayed in an ordinary image of lung P.

FIG. 13 illustrates an example table that relates resection tools and their extents of resections to display methods of boundary lines.

FIG. 14 illustrate a display example of a boundary of a surgical margin corresponding to a stapler.

DESCRIPTION OF THE PREFERRED EMBODIMENTS

Figure 1:
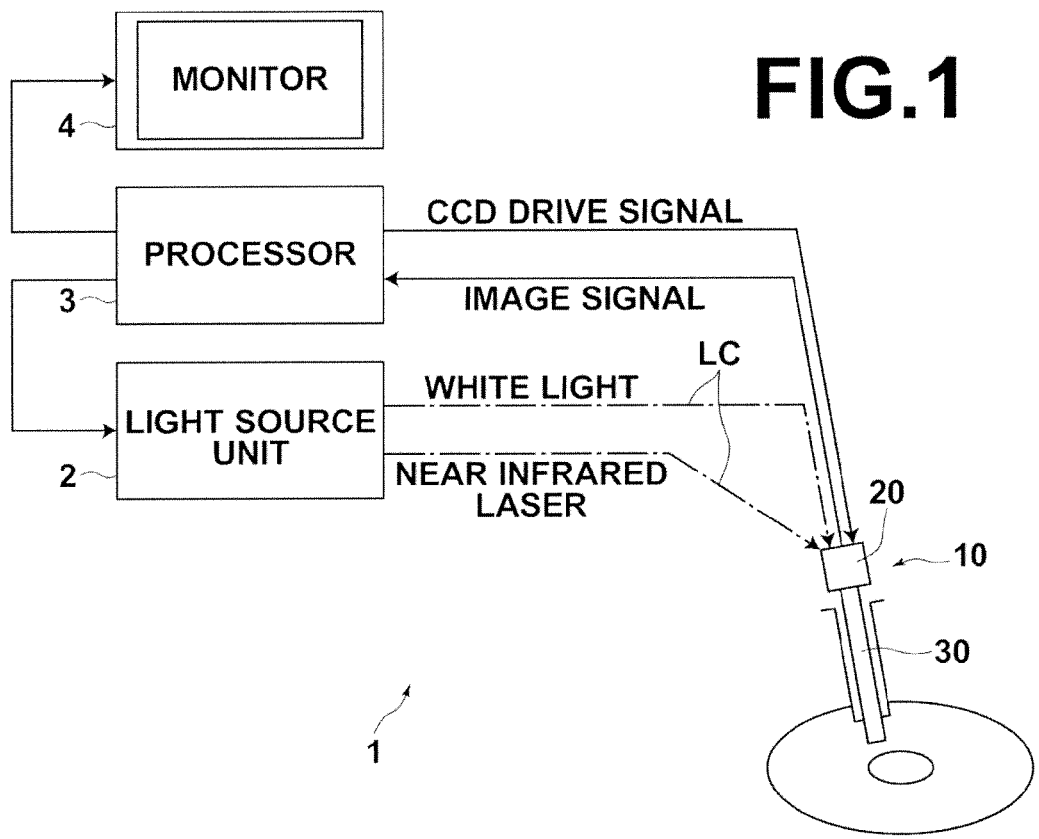
FIG. 1 is an overview of a rigid endoscope system that employs an embodiment of a fluorescence endoscope apparatus of the present invention, illustrating a schematic configuration thereof.

Hereinafter, a rigid endoscope system that employs an embodiment of an image capturing and display apparatus of the present invention will be described in detail with reference to the accompanying drawings. FIG. 1 is an overview of rigid endoscope system 1 of the present embodiment, illustrating a schematic configuration thereof. The present embodiment has a characteristic feature in displaying a surgical margin, but an overall system configuration will be described first. FIG. 1 is an overview of rigid endoscope system 1, illustrating a schematic configuration thereof.

As illustrated in FIG. 1, rigid endoscope system 1 of the present embodiment includes light source unit 2 for emitting blue light and near infrared light, rigid endoscope imaging device 10 for projecting white light obtained by converting blue light emitted from light source unit 2 and near infrared light to an observation area and capturing an ordinary image based on reflection light reflected, by the projection of the white light, from the observation area and a fluorescence image based on fluorescence emitted, by the projection of the near infrared light, from the observation area, processor 3 for performing predetermined processing on an image signal obtained by rigid endoscope imaging device 10 and outputting a control signal to light source unit 2, and monitor 4 for displaying the fluorescence image and ordinary image of the observation area based on a display control signal generated by processor 3.

As shown in FIG. 1, rigid endoscope imaging device 10 includes body cavity insertion section 30 to be inserted into a body cavity, such as an abdominal cavity or a chest cavity, and imaging unit 20 for capturing an ordinary image and a florescence image of the observation area guided by the body cavity insertion section 30.

Figure 2:
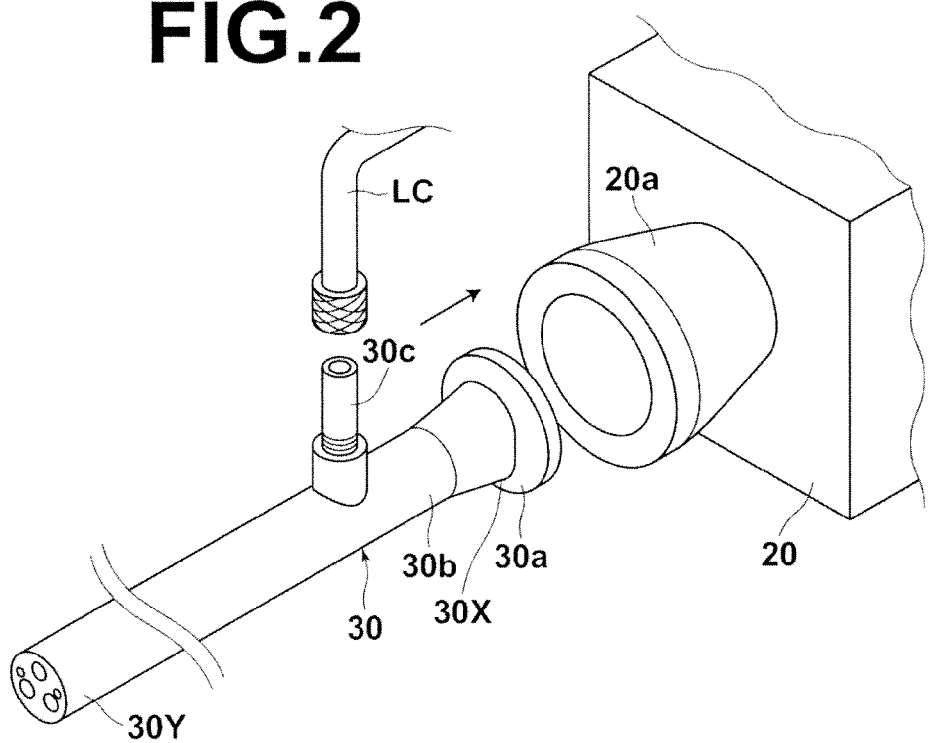
FIG. 2 is a schematic configuration diagram of the body cavity insertion section shown in FIG. 1.

As shown in FIG. 2, body cavity insertion section 30 and imaging unit 20 are detachably connected. Body cavity insertion section 30 includes connection member 30a, insertion member 30b, and cable connection port 30c.

Connection member 30a is provided at proximal end 30X of body cavity insertion section 30 (insertion member 30b) and imaging unit 20 and body cavity insertion section 30 are detachably connected by fitting connection member 30a into, for example, aperture 20a formed in imaging unit 20.

Insertion member 30b is a member to be inserted into a body cavity when imaging is performed in the body cavity. Insertion member 30b is formed of a rigid material and has, for example, a cylindrical shape with a diameter of about 5 mm. Insertion member 30b accommodates inside thereof a group of lenses for forming an image of an observation area, and an ordinary image and a fluorescence image of the observation area inputted from distal end 30Y are inputted, through the group of lenses, to imaging unit 20 on the side of proximal end 30X.

Cable connection port 30c is provided on the side surface of insertion member 30b and an optical cable LC is mechanically connected to the port. This causes light source unit 2 and insertion member 30b to be optically linked through the optical cable LC.

Figure 3:
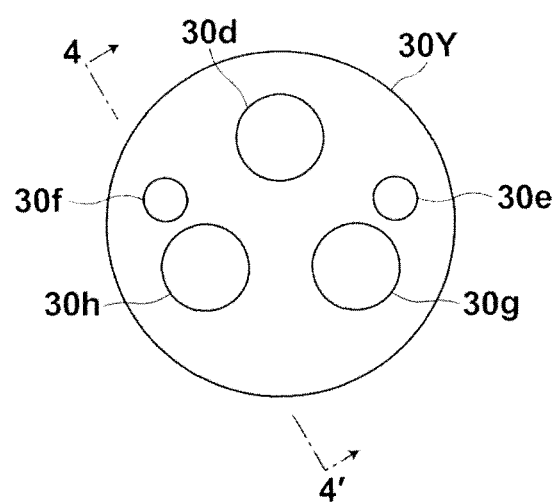
FIG. 3 a schematic view of a distal end portion of the body cavity insertion section.

FIG. 3 illustrates a configuration of distal end 30Y of body cavity insertion section 30. As shown in FIG. 3, imaging lens 30d is provided in the approximate center of distal end 30Y of body cavity insertion section 30 for forming an ordinary image and a fluorescence image, and white light projection lenses 30e, 30f for projecting white light and near infrared light projection lenses 30g, 30h for projecting near infrared light are respectively provided substantially symmetrically across the imaging lens 30d. The reason why each pair of two white light projection lenses 30e, 30f and near infrared light projection lenses 30g, 30h is provide symmetrically with respect to imaging lens 30d is to prevent a shadow from being formed in an ordinary image and a fluorescence image due to irregularity of the observation area.

Figure 4:
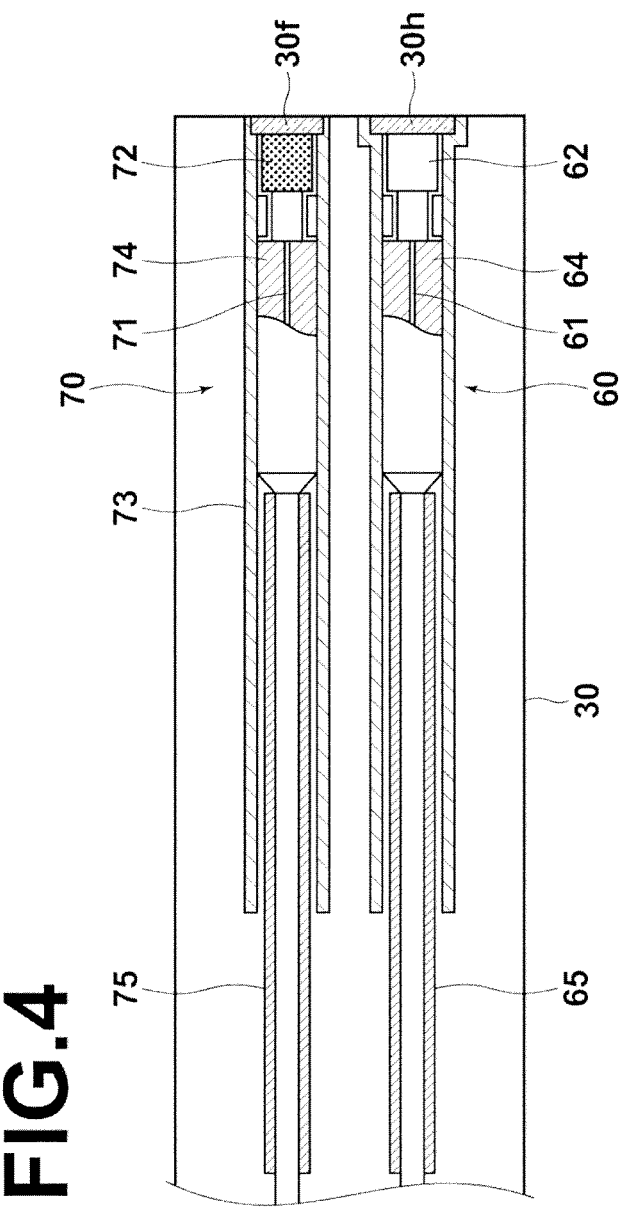
FIG. 4 is a cross-sectional view taken along the line 4-4' in FIG. 3.

FIG. 4 is a cross-sectional view taken along the line 4'-4' in FIG. 3. As illustrated in FIG. 4, body cavity insertion section 30 includes inside thereof white light projection unit 70 and near infrared light projection unit 60.

White light projection unit 70 includes multimode optical fiber 71 for guiding blue light and fluorescent body 72 which is excited and emits visible light of green to yellow by absorbing a portion of the blue light guided through multimode optical fiber 71. Fluorescent body 72 is formed of a plurality of types of fluorescent materials, such as a YAG fluorescent material, BAM ($BaMgAl_{10}O_{17}$), and the like.

Tubular sleeve member 73 is provided so as to cover the periphery of fluorescent body 72, and ferrule 74 for holding multimode optical fiber 71 at the central axis is inserted in sleeve member 73. Further, flexible sleeve 75 is inserted between sleeve member 73 and multimode optical fiber 71 extending from the proximal side (opposite to the distal side) of ferrule 74 to cover the jacket of the fiber.

Near infrared light projection unit 60 includes multimode optical fiber 61 for guiding near infrared light, and space 62 is provided between multimode optical fiber 61 and near infrared light projection lens 30*h*.

Also near infrared light projection unit 60 is provided with tubular sleeve member 63 covering the periphery of space 62, in addition to ferrule 64 and flexible sleeve 65, as in white light projection unit 70.

As for the multimode optical fiber used in each light projection unit, for example, a thin optical fiber with a core diameter of 105 μm, a clad diameter of 125 μm, and an overall diameter, including a protective outer jacket, of 0.3 mm to 0.5 mm may be used.

Here, the structures of white light projection unit 70 having white light projection lens 30*f* and near infrared light projection unit 60 having near infrared light projection lens 30*h* have been described. Note that white light projection unit having white light projection lens 30*e* and near infrared light projection unit having near infrared light projection lens 30*g* have identical structures to those of the aforementioned units respectively.

Figure 5:
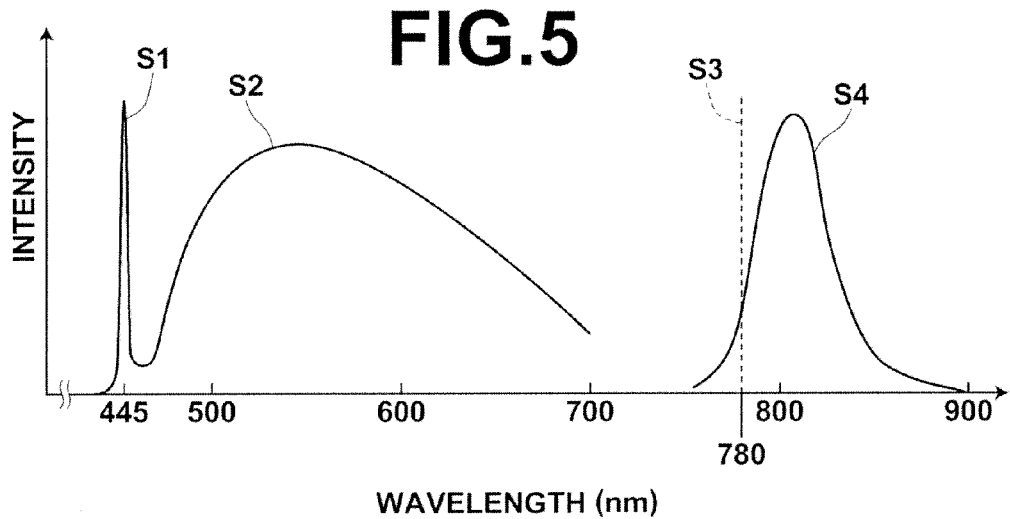
FIG. 5 illustrates a spectrum of light outputted from each light projection unit of the body cavity insertion section, and spectra of fluorescence and reflection light emitted/reflected from an observation area illuminated by the light.

Each spectrum of light projected onto the observation area from each light projection unit, and spectra of fluorescence and reflection light emitted/reflected from the observation area by the projection of the light are shown in FIG. 5. FIG. 5 shows a blue light spectrum S1 projected through fluorescent body 72 of white light projection unit 70, a green to yellow visible light spectrum S2 excited and emitted from fluorescent body 72 of white light projection unit 70, a near infrared light spectrum S3 projected from near infrared light projection unit 60, and an ICG spectrum S4 emitted by the projection of the near infrared light spectrum S3 from near infrared light projection unit 60.

The term "white light" as used herein is not strictly limited to light having all wavelength components of visible light and may include any light as long as it includes light in a specific wavelength range, for example, primary light of R (red), G (green), or B (blue).

Thus, in a broad sense, the white light may include, for example, light having wavelength components from green to red, light having wavelength components from blue to green, and the like. Although white light projection unit 70 projects the blue light spectrum S1 and visible light spectrum S2 shown in FIG. 5, the light of these spectra is also regarded as white light.

Figure 6:
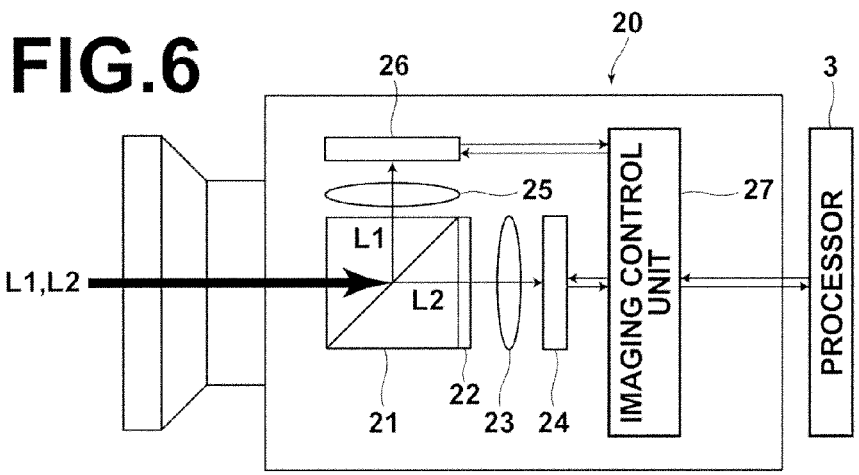
FIG. 6 is a schematic configuration diagram of an imaging unit.

FIG. 6 illustrates a schematic configuration of imaging unit 20. Imaging unit 20 includes a first imaging system for imaging a fluorescence image of an observation area formed by the group of lens in body cavity insertion section 30 to generate an ICG fluorescence image signal of the observation area, and a second imaging system for imaging an ordinary image of the observation area formed by the group of lens in body cavity insertion section 30 to generate an image signal of the observation area. These imaging systems are separated into two orthogonal optical axes by dichroic prism 21 having a spectral characteristic that reflects an ordinary image and transmits a fluorescence image.

The first imaging system includes near infrared light cut filter 22 that transmits a fluorescence image outputted from body cavity insertion section 30 and cuts near infrared light, first image forming optical system 23 that forms a fluorescence image L2 outputted from body cavity insertion section 30 and transmitted through dichroic prism 21 and near infrared light cut filter 22, and high sensitivity image sensor 24 that captures the fluorescence image L2 formed by first image forming optical system 23.

The second imaging system includes second image forming optical system 25 that forms an ordinary image L1 outputted from body cavity insertion section 30 and reflected from dichroic prism 21 and image sensor 26 that captures the ordinary image L1 formed by second image forming optical system 25.

High sensitivity image sensor 24 detects light in a wavelength range of fluorescence image L2 with high sensitivity, converts the detected light to a fluorescence image signal, and outputs the fluorescence image signal. High sensitivity image sensor 24 is a monochrome image sensor.

Image sensor 26 detects light in the wavelength of ordinary image L1, converts the detected light to an ordinary image signal, and outputs the image signal. Color filters of three primary colors, red (R), green (G), and blue (B) are arranged on the imaging surface of image sensor 26 in a Beyer or honeycomb pattern.

Figure 7:
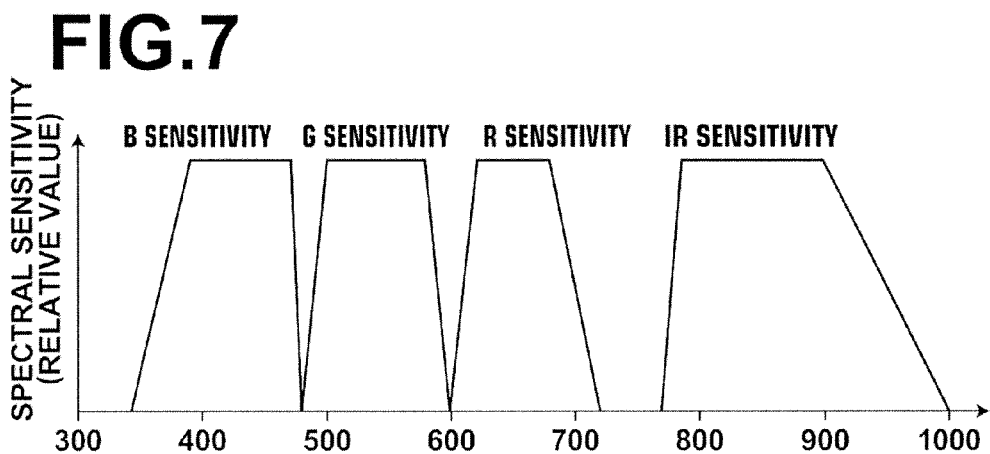
FIG. 7 illustrates spectral sensitivity of the imaging unit.

FIG. 7 is a graph of spectral sensitivity of imaging unit 20. More specifically, imaging unit 20 is configured such that the first imaging system has IR (near infrared) sensitivity, the second imaging system has R (red) sensitivity, G (green) sensitivity, and B (blue) sensitivity.

Imaging unit 20 further includes imaging control unit 27. Imaging control unit 27 controls high sensitivity image sensors 24 and image sensor 26 based on a CCD drive signal outputted from processor 3, performs CDS/AGC (correlated double sampling/automatic gain control) and A/D conversion on a fluorescence image signal outputted from high sensitivity image sensor 24 and an ordinary image signal outputted from image sensor 26, and outputs resultant image signals to processor 3 through a cable.

Figure 8:
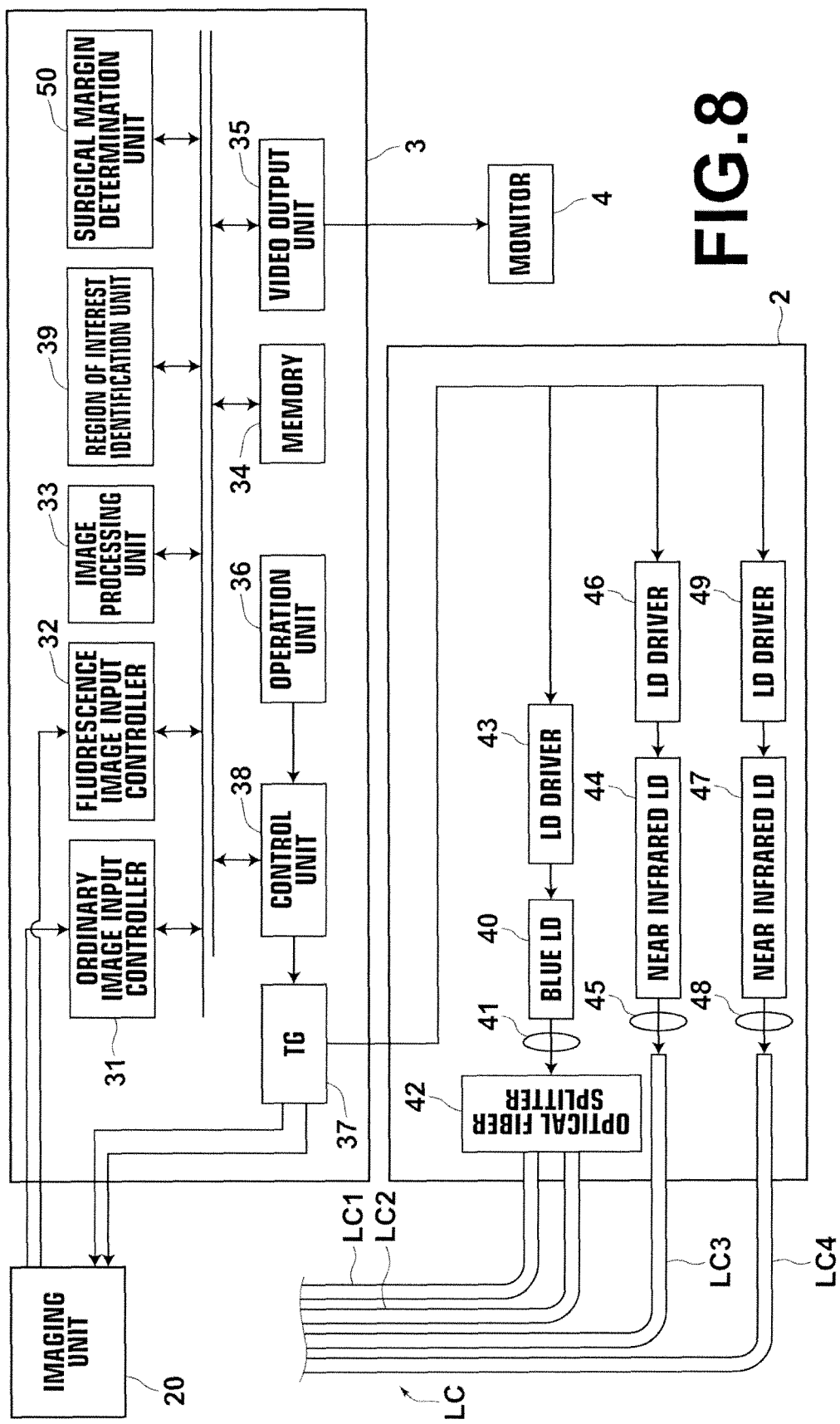
FIG. 8 is a block diagram of an image processing unit and a light source unit, illustrating schematic configurations thereof.

FIG. 8 is a block diagram of light source unit 2 and processor 3, illustrating schematic configurations thereof. As shown in FIG. 8, processor 3 includes ordinary image input controller 31, fluorescence image input controller 32, image processing unit 33, memory 34, video output unit 35, operation unit 36, TG (timing generator) 37, control unit 38, region of interest identification unit 39, and surgical margin determination unit 50.

Ordinary image input controller 31 and fluorescence image input controller 32, each provided with a line buffer having a predetermined capacity, temporarily store ordinary image signals and fluorescence image signals with respect to each frame outputted from imaging control unit 27 of imaging unit 20 respectively. Then, the ordinary image signals stored in ordinary image input controller 31 and the fluorescence image signals stored in fluorescence image input controller 32 are stored in memory 34 via the bus.

Image processing unit 33 receives ordinary image signals and fluorescence image signals from memory 34 with respect to each frame, performs predetermined processing on these image signals, and outputs the resultant image signals to the bus.

Video output unit 35 receives ordinary image signals and fluorescence image signals outputted from image processing unit 33 via the bus, generates a display control signal by performing predetermine processing on the received signals, and outputs the display control signal to monitor 4.

Operation unit 36 receives input from the operator, such as various types of operational instructions and control parameters.

Operation unit 36 of the present embodiment, in particular, receives information of an imaging region of a living body, which is an observation area, and information of resection tool for resecting the observation area.

TG 37 outputs drive pulse signals for driving high sensitivity image sensor 24 and image sensor 26 of imaging unit 20, and LD drivers 43, 46, and 49 of light source unit 2, to be described later.

Control Unit 38 performs overall control of the system. In the present embodiment, in particular, control unit 38 includes display control unit 38a, which causes a boundary line of a region in an ordinary image corresponding to a region of interest determined by region of interest identification unit 39 based on a fluorescence image and a boundary line of an area which includes the region in the ordinary image and a predetermined margin added to the region to be displayed in the ordinary image. The display method of these boundary lines will be described later in detail.

Region of interest identification unit 39 identifies a region of interest in the fluorescence image based on the fluorescence image signals obtained by high sensitivity image sensor 24 of imaging unit 20. More specifically, in the present embodiment, section information based on biological information of the observation area is set in region of interest identification unit 39 in advance, and region of interest identification unit 39 identifies a fluorescence portion of the fluorescence image and identifies a section which includes the fluorescence portion as a region of interest. The term "section" as used herein refers to a divided region medically determined based on biological information, such as blood vessel, lymphatic vessel, bronchus, and the like, and sections are provided for lung, liver, and the like. It is assumed here that region of interest identification unit 39 identifies, based on information of imaging region, such as apex of lung received by operation unit 36, a section by performing, for example, a pattern recognition according to the imaging region.

In the present embodiment, the section is determined automatically as described above, but and an arrangement may be adopted in which the section is determined by a doctor or the like by specifying the section in a fluorescence image based on a fluorescence portion of the fluorescence image using operation unit 36.

Further, in the present embodiment, the aforementioned section is identified as a region of interest. But, for example, a prescribed range which includes a fluorescence portion in a fluorescence image may be automatically set as a region of interest or any region of interest may be specified in a fluorescence image by a doctor or the like using operation unit 36. Further, an automatically detected tumor lesion site may be identified as a region of interest.

Surgical margin determination unit 50 determines a boundary line of an area which includes a region in an ordinary image corresponding to a region of interest identified by region of interest identification unit 39 and a surgical margin added to the region.

An example method for calculating a region in an ordinary image corresponding to a region of interest in a fluorescence image identified by region of interest identification unit 39 will be described.

Figures 9, 10:
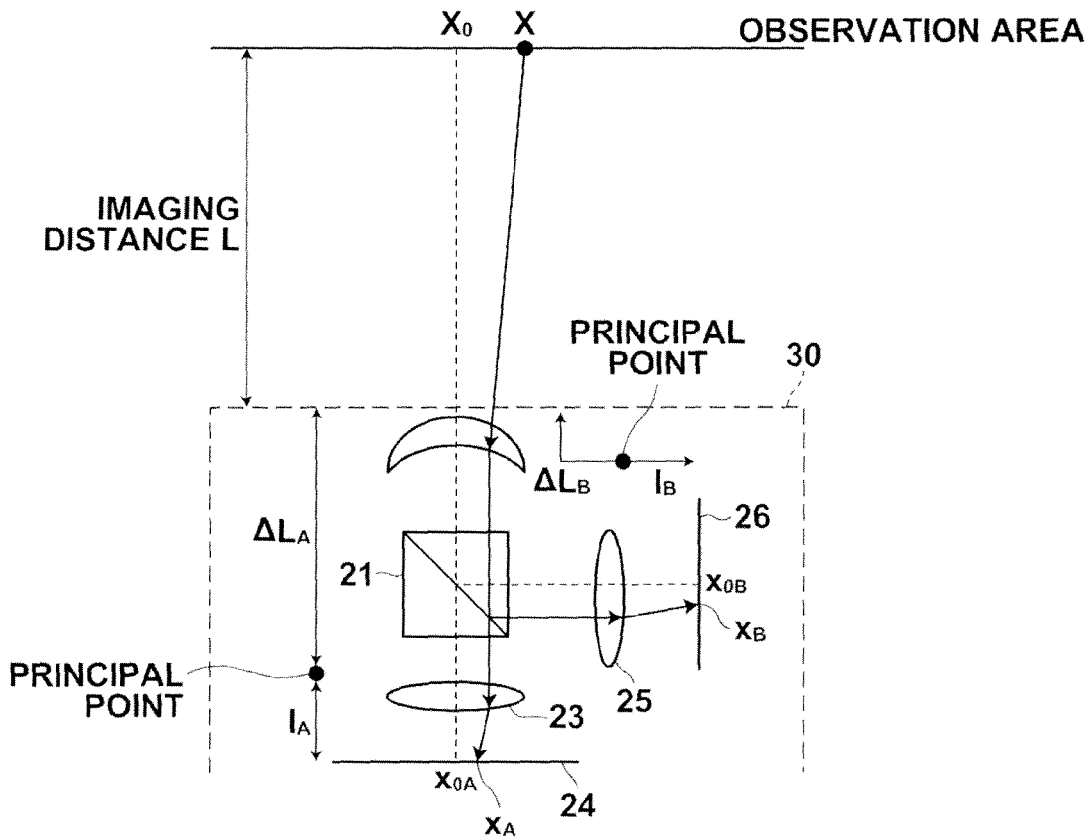
FIG. 9 illustrates how to calculate an area in an ordinary image corresponding to a region of interest identified in a fluorescence image.
FIG. 10 illustrates an example table that relates imaging target regions to surgical margins.

FIG. 9 illustrates positional relationship between the first and second imaging systems when the distance between the distal end of body cavity insertion section 30 and the observation area is L.

When the first and second imaging systems are in the positional relationship illustrated in FIG. 9 and if, for example, a coordinate position on high sensitivity image sensor 24 corresponding to a region of interest identified in the fluorescence image is $X_A$ in FIG. 9, a coordinate position $X_B$ on image sensor 26 where the same point as the region of interest is formed may be calculated by the formula given below.

$$X_B = \frac{m_B}{m_A}(X_A - X_{0A}) + X_{0B} \quad \text{[Formula 1]}$$

$$m_A = \frac{l_A}{L + \Delta L_A} \quad m_B = \frac{l_B}{L + \Delta L_B}$$

where, $\Delta L_A$ is a distance from the distal end of body cavity insertion section 30 to the principal point of the first image forming optical system 23, $\Delta L_B$ is a distance from the distal end of body cavity insertion section 30 to second image forming optical system 25, $l_A$ is a distance from the principal point of first image forming optical system 23 to high sensitivity image sensor 24, $l_B$ is a distance from the principal point of second image forming optical system 25 to image sensor 26, $X_{OA}$ is an optical axis position of the first imaging system, and $X_{OB}$ is an optical axis position of the second imaging system, which are determined in advance as described above. Imaging distance L may be set in advance or may be actually measured by providing a distance measurement means on the distal end of body cavity insertion section 30. It is assumed that the range of the imaging distance has a sufficient depth of field.

It is also assumed that correlation between the coordinate of fluorescence image and coordinate on high sensitivity image sensor 24 is known, and correlation between the coordinate of ordinary image and coordinate on image sensor 26 is known.

Surgical margin determination unit 50 obtains position information of a region in the ordinary image based on coordinate position $X_B$ of image sensor 26 calculated by the formula above. Here, the description has been made only in x directions, but the same applies to y directions.

Surgical margin determination unit 50 determines a boundary line of an area which includes the region in the ordinary image calculated in the manner described above and a surgical margin added to the region. It is assumed that the length of the surgical margin is set in advance. More specifically, in the present embodiment, a table that relates imaging target regions to surgical margins is provided in advance, as shown in FIG. 10, and surgical margin determination unit 50 obtains a length of the surgical margin based on information of imaging region inputted by a doctor or the like using operation unit 36 and the table described above. Acquisition of the surgical margin according to the imaging region in the manner described above allows acquisition of a surgical margin according to surgical guidelines of each region.

Then, surgical margin determination unit 50 obtains coordinate values of the boundary line of the surgical margin in the ordinary image based on a marker image signal included in an ordinary image signal captured by image sensor 26 of imaging unit 20 and the length of the surgical margin obtained in the manner described above. More specifically, the marker image signal described above is a signal obtained by capturing a length measurement marker having preset length information by image sensor 26 together with the observation area, and surgical margin determination unit 50 calculates coordinate values of the boundary line of the surgical margin in the ordinary image such that the ratio between the length information of the length measurement marker and the length of the marker image signal and the ratio between the length of the surgical margin obtained in the manner described above and the length of the surgical margin in the ordinary image correspond to each other.

In this way, by the use of the marker image of the length measurement marker, the length of the surgical margin in the ordinary image may be obtained easily.

For example, the length measurement marker described above is placed on or adjacent to an observation area within an imaging range of image sensor 26. Preferably, the length measurement marker has a blue or green color which is in complementary relationship to the color of an internal organ. This causes the contour of the marker to be more clearly displayed and allows more accurate measurement.

Preferably, the length measurement marker is made of a bioabsorbable material. As for the bioabsorbable material, any known material may be used.

As shown in FIG. 8, light source unit 2 includes blue LD light source 40 that emits blue light with a wavelength of 445 nm, condenser lens 41 that condenses the blue light emitted from blue LD light source 40 and inputs the condensed blue light to optical fiber splitter 42, optical fiber splitter 42 that inputs the received blue light to optical cables LC1, LC2 at the same time, and LD driver 43 that drives blue LD light source 40.

Optical fiber cables LC1, LC2 are optically coupled to multimode optical fibers 71 of white light projection units 70.

Light source unit 2 further includes a plurality of near infrared LD light sources 44, 47 that emits 750 to 790 nm near infrared light, a plurality of condenser lenses 45, 48 that condenses near infrared light emitted from each of infrared LD light sources 44, 47 and inputs the condensed near infrared light to optical fibers LC3, LC4, and a plurality of LD drivers 46, 49 that drives each of infrared LD light sources 44, 47.

Optical fiber cables LC3, LC4 are optically coupled to multimode optical fibers 61 of near infrared light projection units 60.

In the present embodiment, infrared light is used as the excitation light, but the excitation light is not limited to near infrared light and excitation light may be determined according to the type of fluorescent pigment administered to the subject or the type of living tissue for autofluorescence.

Figure 11:
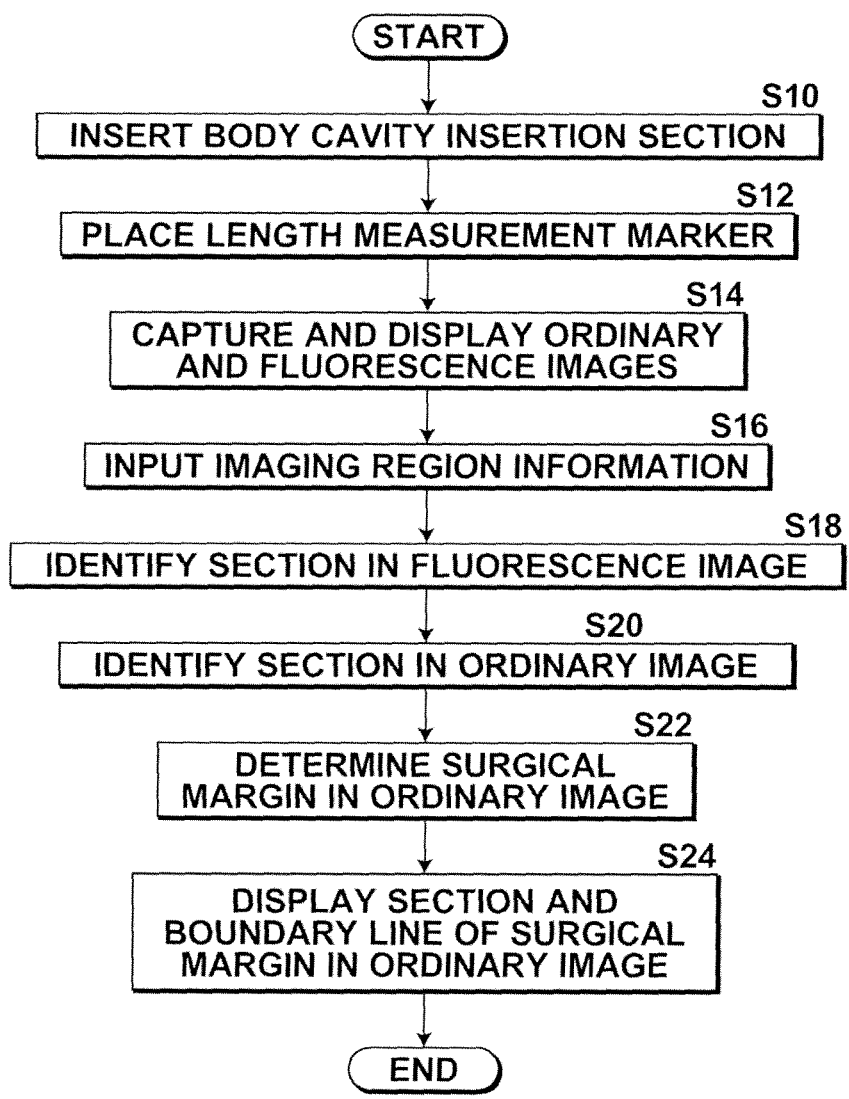
FIG. 11 is a flowchart for describing an operation of the rigid endoscope system that employs an embodiment of the fluorescence endoscope apparatus of the present invention.

An operation of the rigid endoscope system of the present invention will now be described with reference to the flowchart of FIG. 11.

First, body cavity insertion section 30 is inserted into a body cavity of a subject and the distal end of body cavity insertion section 30 is placed adjacent to an observation area (S10). Then, a length measurement marker is placed on an observation area (S12).

Next, an ordinary image and a fluorescence image are captured and the captured images are displayed (S14).

Here, an operation of the system for capturing and displaying an ordinary image is as follows. First, blue light emitted from blue LD light source 40 of light source unit 2 is inputted to optical cables LC1, LC2 simultaneously through condenser lens 41 and optical fiber splitter 42. Then, the blue light is guided through optical cables LC1, LC2 and inputted to body cavity insertion section 30, and further guided through multimode optical fibers 71 of white light projection units 70 in body cavity insertion section 30. Thereafter, a certain portion of the blue light outputted from the output end of each multimode optical fiber 71 is transmitted through fluorescent body 72 and projected onto the observation area, while the remaining portion of the blue light other than the certain portion is subjected to wavelength conversion to green to yellow visible light by fluorescent body 72 and projected onto the observation area. That is, the observation area is illuminated by white light formed of the blue light and green to yellow visible light.

Then, an ordinary image reflected, by the projection of the white light, from the observation area is inputted to imaging lens 30d of distal end 30Y of insertion member 30b, then guided by the group of lenses inside of insertion member 30b, and outputted to imaging unit 20.

The ordinary image inputted to imaging unit 20 is reflected in a right angle direction by dichroic prism 21, then formed on the imaging surface of image sensor 26 by second image forming system 25, and captured by image sensor 26.

Then, R, G, and B image signals outputted from image sensor 26 are subjected to CDS/AGC (correlated double sampling/automatic gain control) and A/D conversion in imaging control unit 27 and outputted to processor 3 through cable 5.

Then, the ordinary image signal inputted to processor 3 is temporarily stored in ordinary image input controller 31 and then stored in memory 34. Ordinary image signals read out from memory 34 with respect to each frame are subjected to tone correction and sharpness correction in image processing unit 33, and sequentially outputted to video output unit 35.

Video output unit 35 generates a display control signal by performing predetermined processing on the inputted ordinary image signal and sequentially outputs display control signals to monitor 4 with respect to each frame. Monitor 4 displays an ordinary image based on the inputted display control signals.

In the mean time, an operation of the system for capturing and displaying a fluorescence image is as follows. First, near infrared light emitted from near infrared LD light sources 44, 47 of light source 2 is inputted to optical cables LC3, LC4 through condenser lenses 45, 48. Then near infrared light is inputted to body cavity insertion section 30 through optical cables LC3, LC4 and guided through multimode optical fibers 61 of near infrared light projection units 60 in body cavity insertion section 30 and projected onto the observation area.

Then, an ICG image emitted, by the projection of the excitation light of near infrared light, from the observation area is inputted to imaging lens 30d of distal end 30Y of insertion member 30b, then guided by the group of lenses inside of insertion member 30b, and outputted to imaging unit 20.

The ICG image inputted to imaging unit 20 is transmitted through dichroic prism 21 and near infrared light cut filter 22, then formed on the imaging surface of high sensitivity image sensor 24 by first image forming optical system 23. The fluorescence image outputted from high sensitivity image sensor 24 is subjected to CDS/AGC (correlated double sampling/automatic gain control) and A/D conversion in imaging control unit 27 and outputted to processor 3 through cable 5.

Then, the fluorescence image signal inputted to processor 3 is temporarily stored in fluorescence image input controller 32 and then stored in memory 34. Florescence image signals read out from memory 34 with respect to each frame are subjected to predetermined image processing in image processing unit 33, and sequentially outputted to video output unit 35.

Video output unit 35 generates a display control signal by performing predetermined processing on the inputted fluorescence image signal and sequentially outputs display control signals to monitor 4 with respect to each frame. Monitor 4 displays a fluorescence image based on the inputted display control signals.

Thereafter, imaging region information is inputted by a doctor or the like using operation unit 36 (S16) and the information is received by region of interest identification unit 39. Then, region of interest identification unit 39 identifies a fluorescence portion of the fluorescence image and identifies a section, including the fluorescence portion, as the region of interest (S20)

The section identified by region of interest identification unit 39 is displayed in the fluorescence image. The drawing on the right in FIG. 12 illustrates an example section identified in a fluorescence image of lung P, i.e., section R1 indicated by diagonal lines.

Next, information of the section in the fluorescence image identified by region of interest identification unit 39 is inputted to surgical margin determination unit 50, and surgical margin determination unit 50 calculates a region in the ordinary image corresponding to the inputted section (S20) and further determines a boundary line of an area which includes the region in the ordinary image and a predetermined surgical margin added to the region (S22).

Then, information of the region in the ordinary image calculated by surgical margin determination unit 50 and information of the boundary line of the area which includes the region and the surgical margin added to the region are outputted to display control unit 38a of control unit 38. Then, based on the inputted information, display control unit 38a causes the region and boundary line of the surgical margin to be displayed in the ordinary image displayed on monitor 4 (S24). The drawing on the left in FIG. 12 illustrates an example display in which section R2 and boundary line SM of a surgical margin are displayed in an ordinary image of lung P. The reference symbol M in the ordinary image represents an image of a length measurement marker, and surgical margin determination unit 50 calculates coordinate values of boundary line SM of the surgical margin in the ordinary image, as described above, based on the image signal of the length measurement marker.

Then, the doctor performs resection of a tumor or the like using a resection tool by observing the boundary line SM of the surgical margin displayed on monitor 4.

Here, when a lesion or the like is resected by a doctor, the cutting section area may vary with the resection tool used by the doctor. Consequently, in the embodiment described above, the boundary line of surgical margin displayed on the ordinary image may be changed according to the type of the resection tool to be used.

More specifically, for example, a table like that shown in FIG. 13 that relates resection tools to display methods of boundary lines corresponding to the cutting section area may be provided in advance. Thereafter, input of information of resection tool may be received from the doctor through operation unit 36, then a boundary line display method may be obtained by referring to the table described above, and the boundary line may be displayed on monitor 4 by the obtained display method corresponding to the resection tool. For example, when the resection tool is an electrosurgical knife, the cutting section is relatively narrow and cutting may be performed along the boundary line of surgical margin, so that a narrow dotted line may be displayed along the boundary line of surgical margin as shown in the drawing on the left in FIG. 12. On the other hand, if the resection tool is a stapler, the cutting section is wider that that of the electrosurgical knife and cutting is performed linearly, so that the boundary line of surgical margin may be displayed with a heavy straight line rather than a narrow dotted line, as shown in FIG. 14. By changing the display form in the manner described above, a cutting section area close to the actual cutting section area may be displayed.

In the embodiment described above, the fluorescence image is captured by the first imaging system, but an image based on light absorption characteristics of the observation area may be captured by projecting special light onto the observation area.

Further, the aforementioned embodiment is an embodiment in which the image capturing and display apparatus of the present invention is applied to a rigid endoscope system, but the apparatus of the present invention may also be applied to other endoscope systems having a soft endoscope. Still further, the apparatus of the present invention is not limited to endoscope applications and may be applied to so-called video camera type medical image capturing systems without any insertion section to be inserted into a body cavity.

What is claimed is:

1. An image acquisition and display method, comprising:
    obtaining an ordinary image captured by projecting illumination light onto an observation area and receiving reflection light reflected from the observation area and a special image captured by projecting special light onto the observation area and receiving light emitted from the observation area, and displaying the obtained ordinary and special images;
    identifying, based on the special image, a prescribed region of interest in the special image;
    determining a boundary line of an area which includes a region in the ordinary image corresponding to the identified region of interest and a predetermined margin added to the region; and
    displaying a boundary line of the region and the boundary line of the area in the ordinary image,
    wherein the obtaining the ordinary image comprises capturing the ordinary image which includes a marker image of a length measurement marker including preset length information, and
    wherein the determining the boundary line comprises determining the predetermined margin based on a size of the marker image.

2. The method of claim 1, wherein said displaying comprises displaying the boundary line of the region within the ordinary image corresponding to the region of interest identified within the special image, and displaying the boundary line of the area which is the region within the ordinary image with the predetermined margin added.

3. The method of claim 1, wherein the boundary line of the margin on the ordinary image is determined such that a ratio of the length information of the length measurement marker to a length of the marker image matches a ratio of a preset length of the margin and a length of the margin within the ordinary image.

4. The method of claim 1, wherein the predetermined margin is determined based on the size of the marker image, when the boundary line having the margin added thereto is displayed on the ordinary image.

5. The method of claim 1, wherein the length measurement marker is imaged along with a subject such that a width of the margin is determined based on the marker image when displaying the boundary line that represents the margin.

6. An image capturing and display apparatus, comprising:
a light projection unit for projecting illumination light and special light onto an observation area;
an imaging unit for imaging an ordinary image by receiving reflection light reflected, by the projection of the illumination light, from the observation area and a special image by receiving light emitted, by the projection of the special light, from the observation area;
a display unit for displaying the ordinary and special images;
a region of interest identification unit for identifying, based on the special image, a prescribed region of interest in the special image; and
a margin determination unit for determining a boundary line of an area which includes a region in the ordinary image corresponding to the identified region of interest and a predetermined margin added to the region,
wherein the display unit displays a boundary line of the region and the boundary line of the area in the ordinary image, and
wherein the imaging unit comprises a unit that captures the ordinary image which includes a marker image of a length measurement marker including preset length information and the margin determination unit comprises a unit that determines the predetermined margin based on a size of the marker image.

7. The apparatus of claim 6, wherein the region of interest identification unit comprises a unit that determines the region of interest based on section information preset based on biological information of the observation area.

8. The apparatus of claim 6, wherein the length measurement marker has a blue or green color.

9. The apparatus of claim 6, wherein the observation area comprises a living body and the length measurement marker comprises a marker comprising a bioabsorbable material and placed on the living body.

10. The apparatus of claim 6, wherein the observation area comprises a living body and the display unit comprises a unit that changes display form of the boundary line of the area according to preset information of resection tool for resecting the living body.

11. The apparatus of claim 10, further comprising a table that relates information of a plurality of resection tools to display forms of the boundary line of the area.

12. The apparatus of claim 6, wherein the light projection unit comprises a unit that projects excitation light as the special light and the imaging unit comprises a unit that captures a fluorescence image as the special image by receiving fluorescence emitted, by the projection of the excitation light, from the observation area.

13. The apparatus of claim 6, wherein display unit displays the boundary line of the region within the ordinary image corresponding to the region of interest identified within the special image, and displays the boundary line of the area which is the region within the ordinary image with the predetermined margin added.

14. The apparatus of claim 6, wherein the boundary line of the margin on the ordinary image is determined such that a ratio of the length information of the length measurement marker to a length of the marker image matches a ratio of a preset length of the margin and a length of the margin within the ordinary image.

15. The apparatus of claim 6, wherein the predetermined margin is determined based on the size of the marker image, when the boundary line having the margin added thereto is displayed on the ordinary image.

16. The apparatus of claim 6, wherein the length measurement marker is imaged along with a subject such that a width of the margin is determined based on the marker image when displaying the boundary line that represents the margin.

17. An image capturing and display apparatus, comprising:
a light projection unit for projecting illumination light and special light onto an observation area;
an imaging unit for imaging an ordinary image by receiving reflection light reflected, by the projection of the illumination light, from the observation area and a special image by receiving light emitted, by the projection of the special light, from the observation area;
a display unit for displaying the ordinary and special images;
a region of interest identification unit for identifying, based on the special image, a prescribed region of interest in the special image; and
a margin determination unit for determining a boundary line of an area which includes a region in the ordinary image corresponding to the identified region of interest and a predetermined margin added to the region,
wherein the display unit displays a boundary line of the region and the boundary line of the area in the ordinary image,
wherein the observation area comprises a living body, and
wherein the margin determination unit includes a plurality of margins corresponding to each of a plurality of types of regions of the living body set in advance, obtains information regarding a region of the living body which is the observation area, and determines a margin corresponding to the region of the living body based on the obtained information regarding the region of the living body.

18. An image acquisition and display method, comprising
obtaining an ordinary image captured by projecting illumination light onto an observation area and receiving reflection light reflected from the observation area and a special image captured by projecting special light onto the observation area and receiving light emitted from the observation area, and displaying the obtained ordinary and special images;
identifying, based on the special image, a prescribed region of interest in the special image;
determining a boundary line of an area which includes a region in the ordinary image corresponding to the identified region of interest and a predetermined margin added to the region; and
displaying a boundary line of the region and the boundary line of the area in the ordinary image,
wherein the observation area comprises a living body, and
wherein the determining the boundary line includes determining a plurality of margins corresponding to each of a plurality of types of regions of the living body set in advance, obtaining information regarding a region of the living body which is the observation area, and determining a margin corresponding to the region of the living body based on the obtained information regarding the region of the living body.

* * * * *